(12) United States Patent
Burge et al.

(10) Patent No.: US 11,231,385 B2
(45) Date of Patent: Jan. 25, 2022

(54) MICROBIAL SENSOR SYSTEM FOR MONITORING THE ENVIRONMENT AND SURFACES

(71) Applicant: Burge Environmental, Inc., Tempe, AZ (US)

(72) Inventors: Scott R. Burge, Tempe, AZ (US); David A. Hoffman, Tempe, AZ (US)

(73) Assignee: Burge Environmental, Inc., Tempe, AZ (US)

( * ) Notice: Subject to any disclaimer, the term of this patent is extended or adjusted under 35 U.S.C. 154(b) by 306 days.

(21) Appl. No.: 16/427,012

(22) Filed: May 30, 2019

(65) Prior Publication Data
US 2019/0369041 A1    Dec. 5, 2019

Related U.S. Application Data

(60) Provisional application No. 62/677,886, filed on May 30, 2018, provisional application No. 62/692,094, filed on Jun. 29, 2018.

(51) Int. Cl.
*G01N 27/327* (2006.01)
*C12Q 1/06* (2006.01)
(Continued)

(52) U.S. Cl.
CPC ......... *G01N 27/327* (2013.01); *A61B 5/1468* (2013.01); *C12Q 1/06* (2013.01); *G01N 27/333* (2013.01); *G01N 33/483* (2013.01)

(58) Field of Classification Search
CPC .......... C12Q 1/04; C12Q 1/06; G01N 27/327; G01N 27/416; G01N 27/403; G01N 27/30; G01N 27/301; G01N 33/483
See application file for complete search history.

(56) References Cited

U.S. PATENT DOCUMENTS

2010/0081014 A1* 4/2010 Tyce .................. H01M 10/441
                                                                429/2
2017/0045470 A1* 2/2017 Burge ................ G01N 27/4035

OTHER PUBLICATIONS

Trinh et al., "Increased generation of electricity in a microbial fuel cell using Geobacter sulferreducens," Korean J. Chem. Eng., 26(3), 748-753 (2009) (Year: 2009).*

(Continued)

*Primary Examiner* — Alexander S Noguerola
(74) *Attorney, Agent, or Firm* — Snell & Wilmer L.L.P.

(57) ABSTRACT

A microbial sensor, system and method that can be used to determine the biochemical conditions of waters, saturated sediments, unsaturated soils, rhizosphere and other environments is disclosed. The flexibility of the microbial sensor design allows for the monitoring of surfaces (skin, ventilation conduits, etc.). An electrochemical microbial sensor system is composed of an indicator electrode(s) and a reference electrode. The reference electrode employs a hydrogen permeable membrane. The electrochemical system is interfaced into a signal/communication module allowing the manual or automated collection of data from field deployments and laboratory investigations. The data is transmitted using various communication technologies including Bluetooth™, cellular, satellite and radio telemetry to cloud-based data management systems. The stored data may be downloaded by users using open-source dashboard and visualization software to image the various environments and/or surfaces investigated.

20 Claims, 3 Drawing Sheets

(51) Int. Cl.
*A61B 5/1468* (2006.01)
*G01N 27/333* (2006.01)
*G01N 33/483* (2006.01)

(56) References Cited

OTHER PUBLICATIONS

Logan et al., Critical Review—Microbial Fuel Cells: Methodology and Technology†, Environmental Science & Technology vol. 40, No. 17, 2006, pp. 5181-5192 (Year: 2006).*

* cited by examiner

MICROBIAL SENSOR SYSTEM FOR MONITORING THE ENVIRONMENT AND SURFACES

CROSS-REFERENCE TO RELATED APPLICATIONS

This application is a non-provisional application and claims the benefit of priority to U.S. Provisional Patent Application No. 62/692,094, filed on Jun. 29, 2018, and U.S. Provisional Patent Application No. 62/677,886, filed on May 30, 2018. The disclosures of each of the provisional applications are incorporated herein by reference to the extent such content does not conflict with the present disclosure.

STATEMENT REGARDING FEDERALLY-SPONSORED RESEARCH OR DEVELOPMENT

This invention was made with government support by the Office of Science grant nos. DE-FOA-0001405 and DE-SC0018495 awarded by the Department of Energy. The government has certain rights in the invention.

FIELD

The present disclosure generally relates to microbial sensors, systems and methods of using the sensors and systems. More particularly, the present disclosure relates to sensors and systems that employ potentiometric (open-circuit voltage and/or recovery voltage) measurements to provide information concerning microbial activity, reduction/oxidation conditions and substrate concentrations of the environment (natural or man-made) or surfaces (walls, ventilation conduits, skin).

BACKGROUND OF THE DISCLOSURE

Microbial fuel cell technology was developed primarily for the conversion of waste products (sewage, farming wastes, etc.) into energy. The use of microbial fuel cells as sensors is less prevalent in the literature. Burge et al., in U.S. Pat. No. 10,113,990 and U.S. patent application Ser. Nos. 15/237,230 and 16/054,789, disclosed microbial sensor systems using open-circuit voltage and recovery voltage as the metric for determining biochemical conditions and substrate concentrations in aqueous and saturated environments.

Microbial fuel cell technology measures and optimizes the flow of electrical current between the electrodes. The measurement circuitry is designed to present almost no impedance to the electrical current. Microbial sensors measure open-circuit voltage using high-impedance measurement circuity. The high-impedance measurement circuitry insures very low current flows between the electrodes.

The electrodes of the microbial fuel cells are known as the anode (source of the electrons) and the cathode (sink of the electrons) for the actively flowing electrical current. In microbial sensors the electrodes are known as the indicator electrode (the electrode exposed to the media to be measured) and the reference electrode. The open-circuit voltage (virtually no current flow) is measured between the indicator and reference electrodes.

Any discussion set forth in this section is for the purpose of providing context for the disclosure. Such discussion should not be taken as an admission that any or all of the discussion constitutes prior art.

SUMMARY OF THE DISCLOSURE

In an aspect, a microbial sensor system is provided comprising: (i) an indicator electrode exposed to a biochemical environment; (ii) a reference electrode comprising a semipermeable electrode that allows diffusion of hydrogen ions; and (iii) a signal communication module electrically connected to the indicator electrode and the reference electrode, wherein the signal communication module is capable of acquiring signals from the indicator electrode and the reference electrode and transmitting the signals to remote users.

In embodiments, the signals comprise open-circuit voltage. In embodiments, the open-circuit voltage corresponds to the biochemical environment. In embodiments, the signals comprise recovery voltage. In embodiments, the recovery voltage corresponds to a substrate concentration in the biochemical environment. In embodiments, the indicator electrode comprises one or more of graphite, graphene, carbon, gold, and platinum. In embodiments, the indicator electrode comprises a biofilm on its surface configured to sense chemicals in the biochemical environment.

In an aspect, a microbial monitoring system is provided comprising: (i) an indicator electrode comprising a biologically active surface; (ii) a reference electrode; (iii) a hydrogen ion-permeable membrane placed in proximity to the reference electrode; (iv) an electronic circuit; and (iv) an indicator electrode wire that conducts electrons from the indicator electrode to the electronic circuit.

In embodiments, the microbial monitoring system further comprises an electrical meter configured to measure potential between the indicator electrode and the reference electrode. In embodiments, the reference electrode comprises a film configured to reduce atmospheric oxygen using electrons produced by the oxidation of substrates on the biologically active surface of the indicator electrode. In embodiments, the film comprises platinum.

In embodiments, the indicator electrode comprises one or more of graphite, graphene, carbon, gold, and platinum.

In embodiments, the electronic circuit is configured to supply a current between the indicator electrode and the reference electrode.

In an aspect, a microbial sensor system is provided, comprising: (i) a reference electrode comprising an ion-permeable membrane, wherein the reference electrode is connected to an electrical cable; (ii) an indicator electrode exposed to a biochemical environment, wherein the indicator electrode is connected to a signal cable; (iii) a measurement circuit, wherein the reference electrode is connected to the measurement circuit via the electrical cable and the indicator electrode is connected to the measurement circuit via the signal cable.

In embodiments, the microbial sensor system further comprises a tube connected to the reference electrode configured to allow direct communication with the atmosphere.

In embodiments, the microbial sensor system further comprises a reference surface connected to the reference electrode. In embodiments, the reference surface is a semipermeable surface that allows the diffusion of hydrogen ions across the surface.

In embodiments, the measurement circuit is configured to measure voltage between the indicator electrode and the reference surface.

In embodiments, the indicator electrode comprises one or more of graphite, graphene, carbon, gold, and platinum. In embodiments, the indicator electrode comprises a biofilm configured to sense chemicals in the biochemical environment.

Primary Components of the Microbial System

In an aspect, a microbial sensing system is an electrochemical analytical system requiring two primary components: 1) an indicator electrode(s), and 2) a reference electrode. In embodiments, the indicator and reference electrodes are electrically connected to a signal acquisition/communication board. In embodiments, the signal board consists of high-impedance potentiometers and circuitry, allowing the collection of potentiometric signals. In embodiments, the data from the signal board is transmitted to a remote user using telemetry, satellite or cellular transmission. In embodiments, the microbial signals are stored on a data logger.

Indicator Electrodes

In an aspect, the indicator electrode is commonly fabricated from graphite, graphene or carbon impregnated polymer materials (e.g., in the form of rods, tubes, or surfaces). In embodiments, other inert materials are used including, for example, gold, platinum, titanium, carbon fabrics and other non-oxidizable materials. In embodiments, the surface of the indicator electrode, after insertion into an environment or onto a surface, becomes populated with a biofilm. In embodiments, the biofilm populating the surface of the indicator electrode oxidizes substrates and/or senses chemicals in its surroundings. In embodiments, the oxidation of the substrates creates a difference in electrochemical potential between the indicator electrode(s) and the reference electrode. In embodiments, the difference in the potential is measured by a high-impedance potentiometer.

In embodiments, the design and fabrication of the indicator electrode is dependent on the application of the microbial monitoring system. In embodiments, an indicator electrode that monitors soils, water and sediments can be rigid structures (e.g., rods or tubes) capable of deployment in natural and man-made environments, while an indicator electrode used to monitor surfaces (e.g., ventilation shafts or skin) can be flexible carbon fabrics or graphene (e.g., sheets or films).

Reference Electrodes

In an aspect, microbial sensor systems employ several types of electrodes as a reference cell. In embodiments, the electrodes are standard reference cells (e.g., silver/silver chloride, calomel, etc.). In embodiments, the electrodes are modified cathode assemblies. In embodiments, the electrodes are indicator electrodes in unchanging environments (e.g., anaerobic environments).

In embodiments, a modified cathode is used as reference for both potentiometric and kinetic measurements. Several designs of cathodes were disclosed in one U.S. Pat. No. 10,113,990 and two U.S. patent application Ser. Nos. 15/237,230 and 16/054,789, each of which are incorporated herein by reference.

In embodiments, the modified cathode is a modified electrode commonly employed in microbial cell technology to serve as the electron acceptor (e.g., a cathode), but the electrode is redesigned for microbial sensing to serve as a reference cell (e.g., an unchanging voltage source) and not as a cathode (e.g., an electron acceptor of electrons produced at the anode). In embodiments, the primary difference is the electrical measurement performed: cathode for measuring current and reference cell for measuring voltage.

In embodiments, reference electrodes disclosed herein include a semipermeable electrode allowing the diffusion of the hydrogen ion. In embodiments, both semipermeable membranes, are used to seal the water in the external environment from introduction into the interior of the electrode. In embodiments, the exchange of the semipermeable membrane is accompanied by a reorientation of the positions of the semipermeable membrane and the carbon fabric within the reference electrode. In embodiments, a reference electrode employing an oxygen permeable membrane requires the membrane to be located between, e.g., the carbon fabric (e.g., an electrical surface) and the body of the reference electrode assembly. In embodiments, a reference electrode employing a hydrogen ion-permeable electrode is positioned between the carbon fabric and the environment under investigation.

Signal/Communication Module

In an aspect, the signal/communication modules are designed to acquire data from the indicator and reference electrodes and transmit the data to remote users. In embodiments, two primary signals are acquired from the indicator and reference electrodes: 1) potentiometric (open-circuit voltage), and 2) kinetic (recovery voltage).

In embodiments, potentiometric signals are the open-circuit voltage (OCV) measured between a reference electrode and each of the indicator electrodes. In embodiments the voltage is measured by high-impedance potentiometers (>10 megaohms for saturated environments and >100 megaohms for dry soils). In embodiments, potentiometric signals are typically used to determine the biochemical environment (potentiometric signal correlates with reduction-oxidation, dissolved oxygen, total dissolved carbon) of the soil profile or rhizosphere under investigation.

In embodiments, kinetic signals are generated by a two-step process. In embodiments, the first step includes electrically connecting an indicator electrode with a cathode allowing the discharge the electrons stored in temporary electron acceptors (cytochromes, etc.) of the biofilm populating the surface of the indicator electrode. In embodiments, the second step terminates the flow of electrons between the indicator electrode and the cathode. After the flow of electrons is terminated, the electrical potential between the anode and cathode increases over time. In embodiments, the electronic circuitry uses a high-impedance potentiometer to measure the increase of electrical potential (recovery voltage) versus time. In embodiments, the change in potential is measured using a three-electrode system: indicator electrode (s), cathode and a reference cell. In embodiments, the electrons are passed between the indicator electrode and the cathode and the change in potential is measured between the indicator electrode and a reference cell. In embodiments, the kinetic signal is used to determine substrate concentration, rate of substrate conversion, and metabolic gas production.

In embodiments, the electrical signals generated by the signal module are transmitted to a remote user through various communication modules including Bluetooth®, radio telemetry, cellular and satellite modems. In embodiments, the cellular modem is used to transmit the data to cloud-based platforms for storage and retrieval of the data by the users. In embodiments, the data is retrieved using open-source dashboards and data visualization websites.

In embodiments, the data may be stored on a data logger located on or adjacent to the electronic boards of the field-deployable systems. In embodiments, the user can physically retrieve the data from the data logger.

Applications of the Data Collected for Field-Deployable or Laboratory-Based Systems In an aspect, the system allows the collection of real-time data or data collected at programmable time intervals (e.g., every 30 minutes, every hour, every day, etc.). In embodiments, the measurement may be obtained manually.

Monitoring of Surfaces

In an aspect, the monitoring of surfaces for electrical potential will allow the determination of the microbial activity at the interface of the surface and the indicator electrode. An example of an application would be to incorporate the sensor system into a bandage for wounds. If the wound becomes septic (anaerobic conditions), the potential difference between the indicator electrode (adjacent to the wound) and the reference electrode (exposed to atmospheric oxygen) will change in response to the bacterial infection. This type of application would be very beneficial for severe burns. In addition, the bandage could be used for persons who have little or no communication skills (very young or old persons, persons in comas, etc.).

BRIEF DESCRIPTION OF THE DRAWING FIGURES

DETAILED DESCRIPTION

In an aspect, microbial sensors are provided. In embodiments, the microbial sensors connect with control/communication circuitry that allows real-time collection and transmission of data using cellular communications to remote users. In embodiments, the data is transmitted to a cloud-based data storage system. In embodiments, the data is accessed by open-source dashboards and data visualizations. In embodiments, the data is used to bioimage the environment and surfaces. In embodiments, in addition to cellular communications, other types of data communication technologies such as Bluetooth®, radio telemetry or satellite may be employed.

In an aspect, described herein are ion-permeable membranes designed for the diffusion of hydrogen ions. Nafion™ is an example of a membrane designed for the transfer of hydrogen ions from one media (anode) to a second media (cathode) in fuel cell (hydrogen or microbial) technologies.

In an aspect, described herein are designs and methods for microbial monitoring systems using a hydrogen ion-permeable membrane in the construction of a reference electrode.

In an aspect, described herein are designs and methods for microbial monitoring systems using hydrogen ion-permeable membranes for the measurement of electrical potentials of surfaces.

Figure 1:
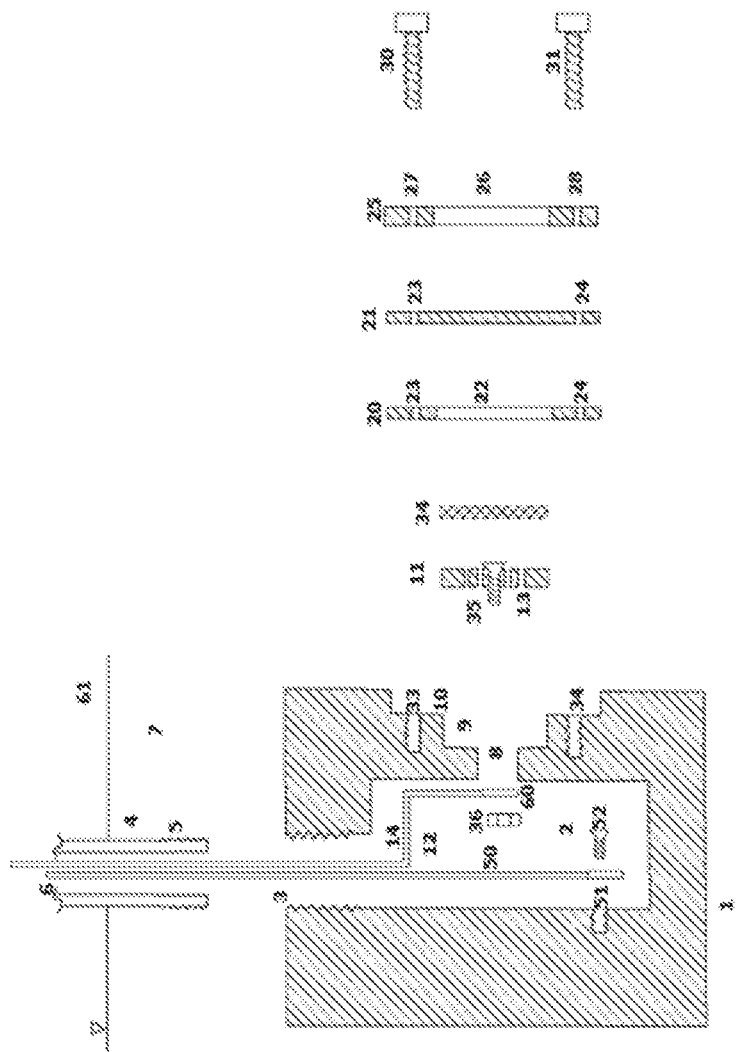
FIG. 1 Illustrates a reference electrode using a hydrogen ion-permeable membrane.

In an aspect, a reference electrode is disclosed as illustrated on FIG. 1. A polymer cathode body 1 is fabricated with a hollow interior 2. The threads 3 of the cathode body 1 connect to a threaded end 5 of a tube 4. Other forms of connection may be used to connect the tube 4 to the reference body 1. The hollow interior 6 of the tube 4 connects with the hollow interior 2 of the reference body 1 to form a pathway allowing a free exchange of atmospheric oxygen 61 with a reference surface 34. The combination of the hollow interior 6 of the tube 4 and the hollow interior of the reference body 2 forms a snorkel.

A reference mounting plate 11 connects to a reference mounting port 9 located on a face of the reference body 1. A screw 35 attaches a reference cable 14 to the reference mounting plate 11 with a nut 36. The screw 35 is in electrical contact with the reference surface 34 and a contact 60 at the end of reference cable. A pattern of small holes 13 pass through the reference mounting plate 11. The pattern of small holes 13 in the reference mounting plate 11 support the reference surface 34 and provide a pathway for atmospheric oxygen 61 to pass from the hollow interior 6 of the reference body 4 through the hollow interior 2 of the cathode body and through port opening 8 to the reference surface 34.

The reference surface 34 is positioned using a reference mounting seal 20 between the reference mounting plate 11, a hydrogen ion-permeable membrane 21 and an exterior plate 25. The reference mounting seal 20, hydrogen ion-permeable membrane 21, and the exterior plate 25 connect within the sealing port 10 of the reference body 1 using mounting screws 30, 31. The mounting screws 30, 31 are passed through the mounting holes 23, 24 of the reference mounting seal 20, the mounting holes 23, 24 of the hydrogen ion-permeable membrane 21, and the mounting holes 27, 28 of the exterior plate 25. The screws 30, 31 are secured to mounting holes 33, 34 located in the sealing port 10 on the cathode body 1. Securing the mounting screws 30, 31 with exterior plate 25, reference mounting seal 20, and hydrogen ion-permeable membrane 21 to the reference body 1 forms a water-proof seal preventing water from the environment 7 from entering the interior 2 of the of the reference body 1.

The hydrogen ion-permeable membrane 21 allows the transfer of hydrogen ions from the surrounding environment 7 through a port 26 located in the exterior plate 25. The reference mounting seal 20 provides for a waterproof seal between the polymer membrane 21 and the reference mounting port 10. The water-proof seal prevents water from the environment 7 entering in the interior 2 of the reference body 1.

A leak detection cable 50 connects to the interior of the reference body 1 with a screw 52 and a threated hole 51. The purpose of the leak detection cable 50 allows the detection of water within the interior 2 of the reference body 1.

Oxygen passes from the atmosphere 61 through the interior 6 of the tube 4 and into the hollow interior 2 of the reference body 1. The oxygen passes from the interior 2 of the reference body 1 port 8 and through the holes 13 of the reference mounting plate 11 and interact with the reference surface 34.

Hydrogen ions from the environment 7 pass through the port 26 of the exterior plate 25 and pass through the hydrogen ion-permeable membrane 21. The ions then pass to the reference surface 34 and interact with the oxygen from the atmosphere 61.

The reference surface 34 is electrically connected to the screw 35. The electrical signal is transferred from the screw 35 to a connector 60 to the reference cable 14. The reference cable 14 transfers the electrical signal through the reference body 1 and the tube 4.

Figure 2:
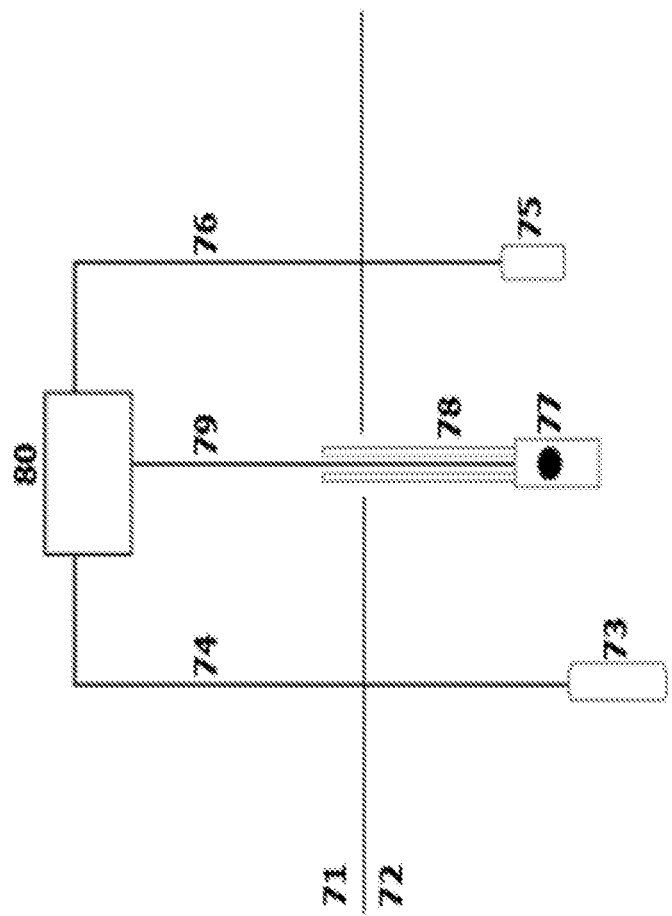
FIG. 2 Illustrates the reference electrode with a hydrogen ion-permeable membrane deployed within a microbial sensor monitoring system for characterizing an environment (natural or manmade).

In an aspect, a reference electrode is disclosed as illustrated in FIG. 2. A reference cell 73 located in the subsurface 72, with an electrical cable 74 connects to a measurement circuit 80. An indicator electrode 75 with a signal cable 76 connects to the measurement circuit 80. A reference cell 77 connects to a tube 78 allowing direct connection with the atmosphere 71 within the interior of the reference cell 77. A reference cable 79 connects the reference 77 with the measurement circuit 80. The electrical potential between the indicator electrode 75 and the reference cell 77 is measured. Multiple indicator electrodes 75 may be used.

The reference cell 77 and reference cable 79 can used to pass a current (periodically) from the indictor electrode 75 to the reference cell 77. The measurement circuit 80 measures the voltage between the indication electrode 73 and the reference surface 77. Alternatively, during kinetic measurements the reference surface 77 is not used as the reference for the measurement potential for kinetic measurements, but a second reference cell 73 is used to measure electrical potential of the indicator electrode 73.

Figure 3:
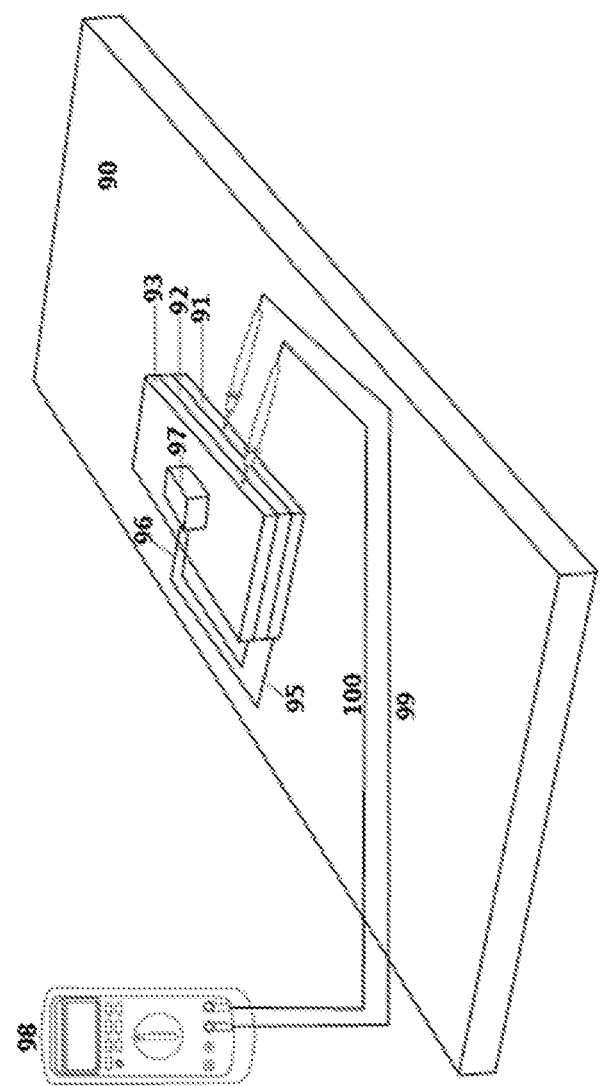
FIG. 3 Illustrates a microbial monitoring system with a hydrogen ion-permeable membrane used for monitoring surfaces.

In an aspect, a microbial monitoring system is disclosed as illustrated in FIG. 3. A measurement system for surfaces 90 including ventilation conduits and skin is illustrated. A thin indicator electrode 91, is bonded or placed in proximity with a hydrogen ion-permeable membrane 92. The hydrogen ion-permeable membrane 92 is bonded or placed in proximity to the reference electrode 93. The indicator electrode 91 is composed of a non-oxidizing, conductive material such as graphite fabric, carbon paper or graphene. The indicator electrode 91 must support the growth and/or measurement of biofilms, microbial communities or other biologically active surfaces while not being oxidized or poisoned by the surface being investigated. The hydrogen ion-specific membrane 92 allows the diffusion of hydrogen ions from the oxidation reactions at the indicator electrode 91 to a reference electrode 93. The materials of the hydrogen ion-specific membrane 92 include Nafion™ and other polymers used to separate anodes and cathodes in fuel cells.

The reference electrode 93 is composed of fabrics and films capable of the reduction of atmospheric oxygen using the electrons produced by the oxidation of substrates by the biofilms, microbes or other biologically active surfaces populating the surface of the indicator electrode 91. An example of materials includes graphite fabrics coated with platinum or other catalyst for the reduction of atmospheric oxygen.

An indicator electrode wire 95 or other conductor conducts the electrons from the indicator electrode 91 to an electronic circuit 97. A reference wire or other conductor 96 conducts the electrons from the reference 93 to the electronic circuit 97. The electronic circuitry 97 measures either potential or current.

Alternatively, an electrical meter 98 is used to manually measure the potential between the indicator electrode 91 and the reference electrode 93 using least 99 and 100.

The electronic circuitry 97 has the ability to impress a current between the indicator electrode 91 and the reference electrode 93 for the purpose of aiding in the healing of wounds of skin.

We claim:

1. A microbial sensor system comprising:
    (i) an indicator electrode exposed to a biochemical environment;
    (ii) a reference electrode; and
    (iii) a signal communication module electrically connected to the indicator electrode and the reference electrode,
    wherein the signal communication module is capable of acquiring signals from the indicator electrode and the reference electrode and transmitting the signals to remote users, and
    wherein the indicator electrode and the reference electrode are bonded to a hydrogen permeable membrane.

2. The microbial sensor system of claim 1, wherein the signals comprise open-circuit voltage.

3. The microbial sensor system of claim 2, wherein the open-circuit voltage corresponds to the biochemical environment.

4. The microbial sensor system of claim 1, wherein the signals comprise recovery voltage.

5. The microbial sensor system of claim 1, wherein the indicator electrode is adjacent a wound, a wall, or a ventilation conduit.

6. The microbial sensor system of claim 1, wherein the indicator electrode comprises one or more of graphite, graphene, carbon, gold, and platinum.

7. The microbial sensor system of claim 1, wherein the indicator electrode comprises a biofilm on its surface configured to sense chemicals in the biochemical environment.

8. A microbial monitoring system comprising:
    (i) an indicator electrode comprising a biologically active surface;
    (ii) a reference electrode;
    (iii) a hydrogen ion-permeable membrane bonded to the indicator electrode and the reference electrode;
    (iv) an electronic circuit; and
    (v) an indicator electrode wire that conducts electrons from the indicator electrode to the electronic circuit.

9. The microbial monitoring system of claim 8, further comprising an electrical meter configured to measure potential between the indicator electrode and the reference electrode.

10. The microbial monitoring system of claim 8, wherein the reference electrode comprises a film.

11. The microbial monitoring system of claim 10, wherein the film comprises platinum.

12. The microbial monitoring system of claim 8, wherein the indicator electrode comprises one or more of graphite, graphene, carbon, gold, and platinum.

13. The microbial monitoring system of claim of claim 8, wherein the indicator electrode comprises flexible carbon fabric.

14. A microbial sensor system, comprising:
    (i) a reference electrode connected to an electrical cable;
    (ii) an indicator electrode exposed to a biochemical environment in a wound,
    wherein the indicator electrode is connected to a signal cable; and
    (iii) a measurement circuit,
    wherein the reference electrode is connected to the measurement circuit via the electrical cable and the indicator electrode is connected to the measurement circuit via the signal cable, and
    wherein the indicator electrode and the reference electrode are bonded to a hydrogen permeable membrane.

15. The microbial sensor system of claim 14 wherein the system monitors the wound for anaerobic conditions.

16. The microbial sensor system of claim 14, wherein the indicator electrode comprises flexible carbon fabric.

17. The microbial sensor system of claim 16, wherein the measurement circuit is configured to measure voltage between the indicator electrode and the reference surface.

18. The microbial sensor system of claim 14, wherein the indicator electrode comprises flexible graphene.

19. The microbial sensor system of claim 14, wherein the indicator electrode comprises one or more of graphite, graphene, carbon, gold, and platinum.

20. The microbial sensor system of claim 14, wherein the indicator electrode comprises a biofilm on its surface configured to sense chemicals in the biochemical environment.

* * * * *